US009515276B2

United States Patent
An et al.

(10) Patent No.: US 9,515,276 B2
(45) Date of Patent: Dec. 6, 2016

(54) ORGANIC X-RAY DETECTOR AND X-RAY SYSTEMS

(71) Applicant: General Electric Company, Schenectady, NY (US)

(72) Inventors: Kwang Hyup An, Rexford, NY (US); Gautam Parthasarathy, Niskayuna, NY (US); Jie Jerry Liu, Niskayuna, NY (US); James Edward Pickett, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 207 days.

(21) Appl. No.: 14/474,761

(22) Filed: Sep. 2, 2014

(65) Prior Publication Data
US 2016/0064680 A1  Mar. 3, 2016

(51) Int. Cl.
*H01L 51/44* (2006.01)
*H01L 27/30* (2006.01)
(Continued)

(52) U.S. Cl.
CPC ............. *H01L 51/448* (2013.01); *G01N 23/04* (2013.01); *G01T 1/2018* (2013.01);
(Continued)

(58) Field of Classification Search
CPC .... H01L 51/448; H01L 51/005; H01L 27/307; H01L 51/0034; H01L 27/308; H01L 51/0032; H01L 51/0036; H01L 51/4253; H01L 51/0039; H01L 51/5259; H01L 51/0043; G01T 1/2018; G01N 23/04
(Continued)

(56) References Cited

U.S. PATENT DOCUMENTS 5,179,284 A * 1/1993 Kingsley ................ B29C 51/16
                                                     250/367
6,455,620 B1    9/2002 Cyr et al.
(Continued)

FOREIGN PATENT DOCUMENTS

EP    1253171 B1   6/2009
EP    2251713 A1   11/2010
EP    2445029 A1   4/2012

OTHER PUBLICATIONS

Li et al., "Development of a simple device for a moisture-proof X-ray diffraction analysis", Journal of Powder Diffraction, Cambridge University Press, Sep. 1997, vol. 12, Issue 03, pp. 145-150.
(Continued)

*Primary Examiner* — David Porta
*Assistant Examiner* — Gisselle Gutierrez
(74) *Attorney, Agent, or Firm* — Mary Louise Stanford

(57) ABSTRACT

An organic x-ray detector is presented. The organic x-ray detector includes a layered structure. The layered structure includes a thin-film transistor (TFT) array disposed on a substrate, an organic photodiode disposed on the TFT array, and a scintillator layer disposed on the organic photodiode. The organic x-ray detector further includes an encapsulation cover at least partially encapsulating the layered structure; and an oxygen getter layer disposed between the organic photodiode and the encapsulation cover, wherein the oxygen getter layer includes an ether-containing material. X-ray system including the organic x-ray detector is also presented.

21 Claims, 6 Drawing Sheets

(51) Int. Cl.
*G01N 23/04* (2006.01)
*H01L 51/00* (2006.01)
*G01T 1/20* (2006.01)
H01L 51/42 (2006.01)
H01L 51/52 (2006.01)

(52) U.S. Cl.
CPC .......... *H01L 27/307* (2013.01); *H01L 27/308* (2013.01); *H01L 51/005* (2013.01); *H01L 51/0032* (2013.01); *H01L 51/0034* (2013.01); H01L 51/0036 (2013.01); H01L 51/0039 (2013.01); H01L 51/0043 (2013.01); H01L 51/4253 (2013.01); H01L 51/5259 (2013.01)

(58) Field of Classification Search
USPC ..................................................... 250/370.11
See application file for complete search history.

(56) References Cited

U.S. PATENT DOCUMENTS

| | | | |
|---|---|---|---|
| 6,642,524 B2 | 11/2003 | Vafi et al. | |
| 6,680,094 B2 | 1/2004 | Kikuchi et al. | |
| 6,982,424 B2 | 1/2006 | Vafi et al. | |
| 7,053,381 B2 | 5/2006 | Shaw et al. | |
| 7,696,722 B2 | 4/2010 | Utschig et al. | |
| 8,053,984 B2 | 11/2011 | Lee et al. | |
| 8,236,727 B2 | 8/2012 | Ohta et al. | |
| 8,415,628 B1 | 4/2013 | Shaw et al. | |
| 8,431,721 B2 | 4/2013 | Deshpande et al. | |
| 8,497,481 B2 | 7/2013 | Shinba et al. | |
| 8,579,506 B2 | 11/2013 | Morton | |
| 8,581,254 B2 | 11/2013 | Couture et al. | |
| 2005/0051757 A1* | 3/2005 | Shepodd ............ | B01D 53/8671 252/181.1 |
| 2006/0163534 A1 | 7/2006 | Sugimoto et al. | |
| 2007/0184300 A1 | 8/2007 | Yokose et al. | |
| 2008/0142721 A1 | 6/2008 | Spahn | |
| 2009/0084961 A1 | 4/2009 | Tonotani et al. | |
| 2010/0207112 A1 | 8/2010 | Furst et al. | |
| 2012/0241628 A1* | 9/2012 | Hesser ................ | G01T 1/2018 250/362 |
| 2012/0318348 A1 | 12/2012 | Frazier et al. | |
| 2013/0199603 A1 | 8/2013 | Snaith et al. | |
| 2014/0027739 A1* | 1/2014 | van de Weijer .... | H01L 51/5256 257/40 |
| 2015/0144889 A1* | 5/2015 | An ........................ | G01T 1/2018 257/40 |
| 2016/0027847 A1* | 1/2016 | Liu ....................... | G01N 23/04 378/62 |
| 2016/0077221 A1* | 3/2016 | Liu ....................... | G01N 23/04 378/62 |

OTHER PUBLICATIONS

Morlat et al.,"Phototransformation of water-soluble polymers. I: photo- and thermooxidation of poly(ethylene oxide) in solid stater",Polymer, ScienceDirect, Jun. 2001, vol. 42, Issue 14, pp. 6071-6079.

Lee et al., "The effect of monomer structure on oxygen inhibition of (meth)acrylates photopolymerization", Polymer, ScienceDirect, Aug. 19, 2004,vol. 45, Issue 18, pp. 6155-6162.

Vacca et al., "Dispensable Getter Materials for lifetime insurance in Organic Electronics", SAES Getters, Organic Electronics : principles, devices and applications, Politecnico di Milano, Nov. 18, 2011, 36 Pages.

Parthasarathy et al., "Organic X-Ray Detector", Pending U.S. Appl. No. 13/955,355, filed Jul. 31, 2013, 22 Pages.

An et al., "Organic X-Ray Detector With Barrier Layer", Pending U.S. Appl. No. 14/087,774, filed Nov. 22, 2013, 16 Pages.

PCT Search Report and Written Opinion issued in connection with corresponding Application No. PCT/US2015/044803 on Nov. 10, 2015.

* cited by examiner

ORGANIC X-RAY DETECTOR AND X-RAY SYSTEMS

BACKGROUND

Embodiments of the invention generally relate to organic x-ray detectors. More particularly, embodiments of the invention relate to organic x-ray detectors including oxygen getter layers.

Digital x-ray detectors fabricated with continuous photodiodes have potential applications for low cost digital radiography as well as for rugged, light-weight and portable detectors. Digital x-ray detectors with continuous photodiodes have an increased fill factor and potentially higher quantum efficiency. The continuous photodiode generally includes organic photodiodes (OPDs). A scintillator which converts x-ray to visible light is generally disposed on top of the OPDs.

Typical organic x-ray detectors are subject to performance degradation upon exposure to oxygen. Possible degradation mechanisms include one or both of oxidation of electrode materials and oxidation of organic materials (e.g., OPD materials). During the post OPD deposition processes, such as, scintillator deposition, encapsulation, laser repair, or operation, OPD has a high chance of exposure to air. Most organic based photodiodes are sensitive to oxygen, and hence need to be protected from the oxygen-containing air.

In conventional packaging (for example in food industry), iron powder is commonly used as an oxygen scavenger. However, iron as an oxygen scavenger may be ineffective since the packaging typically also contains a desiccant, and the oxygen scavenging reaction requires moisture to be efficient. Non-ferrous oxygen scavengers may include cobalt-catalyzed polymers such as Nylon MXD6, which is used in multi-layer packaging. Thus, typical oxygen scavengers may have the disadvantages of being ineffective in anhydrous packaging or of releasing noxious products.

Therefore, there is a need for x-ray detector configurations with improved oxygen getter layers, thereby reducing the oxidation of OPD and/or electrodes.

BRIEF DESCRIPTION

The present invention meets these and other needs by providing an oxygen getter layer in the organic x-ray detector. Accordingly, in one aspect, the invention relates to an organic x-ray detector. The organic x-ray detector includes a layered structure. The layered structure includes a thin-film transistor (TFT) array disposed on a substrate, an organic photodiode disposed on the TFT array, and a scintillator layer disposed on the organic photodiode. The organic x-ray detector further includes an encapsulation cover at least partially encapsulating the layered structure; and an oxygen getter layer disposed between the organic photodiode and the encapsulation cover, wherein the oxygen getter layer includes an ether-containing material.

In another aspect, the invention relates to an organic x-ray detector including a layered structure. The layered structure includes a thin-film transistor (TFT) array disposed on a substrate, an organic photodiode disposed on the TFT array, and a scintillator layer disposed on the organic photodiode. The organic x-ray detector further includes an encapsulation cover at least partially encapsulating the layered structure; and an oxygen getter layer disposed between the organic photodiode and the encapsulation cover, wherein the oxygen getter layer includes a polyether and a transition metal catalyst.

In yet another aspect, the invention relates to an x-ray system. The x-ray system includes an x-ray source; an organic x-ray detector; and a processor operable to process data from the organic x-ray detector. The organic x-ray detector includes a layered structure. The layered structure includes a thin-film transistor (TFT) array disposed on a substrate, an organic photodiode disposed on the TFT array, and a scintillator layer disposed on the organic photodiode. The organic x-ray detector further includes an encapsulation cover at least partially encapsulating the layered structure; and an oxygen getter layer disposed between the organic photodiode and the encapsulation cover, wherein the oxygen getter layer includes an ether-containing material.

These and other features, embodiments, and advantages of the present invention may be understood more readily by reference to the following detailed description.

DRAWINGS

These and other features, aspects, and advantages of the present invention will become better understood when the following detailed description is read with reference to the accompanying drawings, wherein.

DETAILED DESCRIPTION

Figure 1:
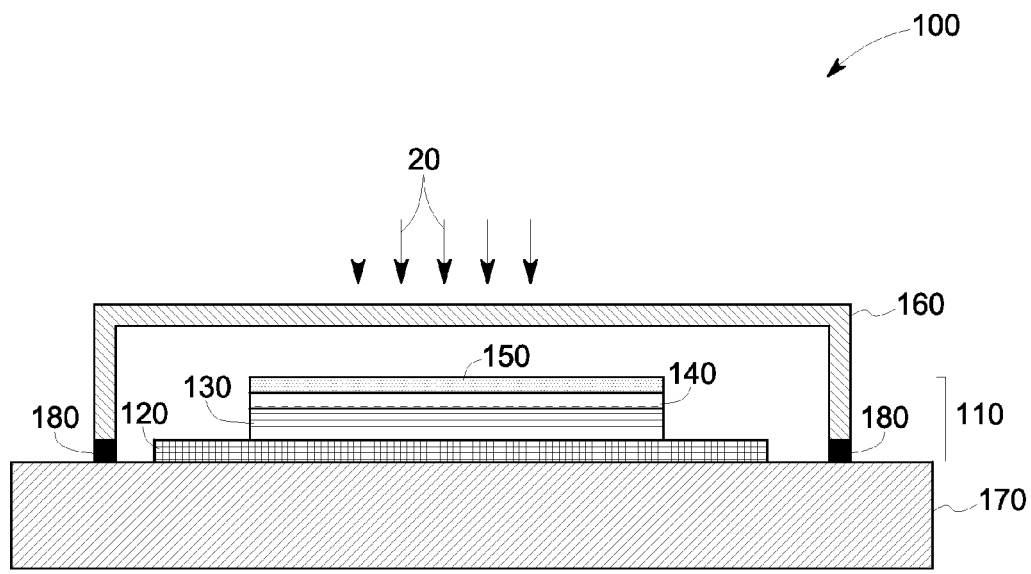
FIG. 1 is a schematic of an organic x-ray detector, according to one embodiment of the invention.

In the following specification and the claims, which follow, reference will be made to a number of terms, which shall be defined to have the following meanings. The singular forms "a", "an" and "the" include plural referents unless the context clearly dictates otherwise. "Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about", and "substantially" is not to be limited to the precise value specified. In some instances, the approximating language may correspond to the precision of an instrument for measuring the value. Similarly, "free" may be used in combination with a term, and may include an insubstantial number, or trace amounts, while still being considered free of the modified term. Here and throughout the specification and claims, range limitations may be combined and/or interchanged, such ranges are identified and include all the sub-ranges contained therein unless context or language indicates otherwise.

As used herein, the term "layer" refers to a material disposed on at least a portion of an underlying surface in a continuous or discontinuous manner. Further, the term "layer" does not necessarily mean a uniform thickness of the disposed material, and the disposed material may have a uniform or a variable thickness. As used herein, the term "disposed on" refers to layers disposed directly in contact with each other or indirectly by having intervening layers there between, unless otherwise specifically indicated. The term "adjacent" as used herein means that the two layers are disposed contiguously and are in direct contact with each other.

In the present disclosure, when a layer is being described as "on" another layer or substrate, it is to be understood that the layers can either be directly contacting each other or have one (or more) layer or feature between the layers. Further, the term "on" describes the relative position of the layers to each other and does not necessarily mean "on top of" since the relative position above or below depends upon the orientation of the device to the viewer. Moreover, the use of "top," "bottom," "above," "below," and variations of these terms is made for convenience, and does not require any particular orientation of the components unless otherwise stated.

One aspect of the invention is to provide an electro-optical device, such as, but not limited to, organic x-ray detectors. A schematic representation of such an organic x-ray detector (XRD) is shown in FIGS. 1-6. As shown in FIGS. 1-6, an organic x-ray detector 100 includes a layered structure 110. The layered structure 110 includes a thin-film transistor (TFT) array 120 disposed on a substrate 170, an organic photodiode 130 disposed on the TFT array 120, and a scintillator layer 140 disposed on the organic photodiode 130. The organic x-ray detector further includes an encapsulation cover 160 at least partially encapsulating the layered structure 110. An oxygen-getter layer 150 is further disposed between the organic photodiode 130 and the encapsulation cover 160.

As illustrated in FIGS. 1-6, the scintillator layer 140 is excited by impinging x-ray radiation 20 and produces visible light. Scintillator layer 140 may be composed of a phosphor material that is capable of converting x-rays to visible light. The wavelength region of light emitted by scintillator layer 140 may range from about 360 nm to about 830 nm. Suitable materials for the layer include, but are not limited to, cesium iodide (CsI), CsI (Tl) (cesium iodide to which thallium has been added) and terbium-activated gadolinium oxysulfide (GOS). Such materials are commercially available in the form of a sheet or screen. Another scintillator that may be used is a PIB (particle in binder) scintillator, where scintillating particles may be incorporated in a binder matrix material and flattened on a substrate. The scintillator layer 140 may be a monolithic scintillator or pixelated scintillator array. The visible light generated by the scintillator layer 140 irradiates an organic photodiode 130 disposed on a TFT array 120.

Figure 7:
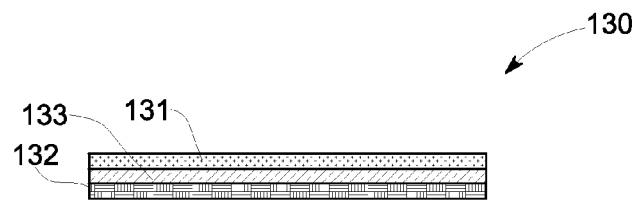
FIG. 7 is a schematic of an organic photodiode, according to one embodiment of the invention.

As shown in FIG. 7, the organic photodiode 130 includes a first electrode 131, a second electrode 132, and an absorber layer (sometimes also referred to as an "active layer") 133 interposed between the first electrode 131 and the second electrode 132. Depending on the application and variations in design, the organic photodiode 130 may include a single organic layer or may include multiple organic layers. The photodiode 130 may also include one or more layers, for example, charge blocking layers and the like (not shown in Figures). Further, the photodiode 130 may be directly disposed on the TFT array 120 or the design may include one or more layers disposed between the photodiode 130 and the TFT array 120.

The absorber layer may be a bulk, hetero-junction organic photodiode layer that absorbs light, separates charge and transports holes and electrons to the contact layers. In some embodiments, the absorber may be patterned. Absorber layer may include a blend of a donor material and an acceptor material; more than one donor or acceptor may be included in the blend. In some embodiments, the donor and acceptor may be incorporated in the same molecule. Further, the HOMO/LUMO levels of the donor and acceptor materials may be compatible with that of the first and second electrodes in order to allow efficient charge extraction without creating an energetic barrier.

Suitable donor materials include low bandgap polymers having LUMO ranging from about 1.9 eV to about 4.9 eV, particularly from 2.5 eV to 4.5 eV, more particularly from 3.0 eV to 4.5 eV; and HOMO ranging from about 2.9 eV to about 7 eV, particularly from 4.0 eV to 6 eV, more particularly from 4.5 eV to 6 eV. The low band gap polymers include conjugated polymers and copolymers composed of units derived from substituted or unsubstituted monoheterocyclic and polyheterocyclic monomers such as thiophene, fluorene, phenylenvinylene, carbazole, pyrrolopyrrole, and fused heteropolycyclic monomers containing the thiophene ring, including, but not limited to, thienothiophene, benzodithiophene, benzothiadiazole, pyrrolothiophene monomers, and substituted analogs thereof. In particular embodiments, the low band gap polymers comprise units derived from substituted or unsubstituted thienothiophene, benzodithiophene, benzothiadiazole, carbazole, isothianaphthene, pyrrole, benzo-bis(thiadiazole), thienopyrazine, fluorene, thiadiazolequinoxaline, or combinations thereof. In the context of the low band gap polymers described herein, the term "units derived from" means that the units are each a residue comprising the monoheterocyclic and polyheterocyclic group, without regard to the substituents present before or during the polymerization; for example, "the low band gap polymers comprise units derived from thienothiophene" means that the low band gap polymers comprise divalent thienothiophenyl groups. Examples of suitable materials for use as low bandgap polymers in the organic x-ray detectors according to the present invention include copolymers derived from substituted or unsubstituted thienothiophene, benzodithiophene, benzothiadiazole or carbazole monomers, and combinations thereof, such as poly[[4,8-bis[(2-ethyl hexyl)oxy]benzo[1,2-b:4,5-b']dithiophene-2,6-diyl][3-fluoro-2-[(2-ethylhexyl)carbonyl]thieno[3,4-b] thiophenediyl (PTB7), 2,1,3-benzothiadiazole-4,7-diyl[4,4-bis(2-ethylhexyl)-4H-cyclopenta[2,1-b:3,4-b']dithiophene-2,6-diyl (PCPDTBT), poly[[9-(1-octylnonyl)-9H-carbazole-2,7-diyl]-2,5-thiophenediyl-2,1,3-benzothiadiazole-4,7-diyl-2,5-thiophenediyl](PCDTBT), poly[(4,40-bis(2-ethylhexyl)dithieno[3,2-b:20,30-d]silole)-2,6-diyl-alt-(2,1,3-benzo-thiadiazole)-4,7-diyl](PSBTBT), poly((4,8-bis (octyloxy)benzo(1,2-b:4,5-b')dithiophene-2,6-diyl)(2-((dodecyloxy)carbonyl) thieno(3,4-b)thiophenediyl)) (PTB1), poly((4,8-bis(octyloxy)benzo(1,2-b:4,5-b')dithiophene-2,6-diyl)(2-((ethylhexyloxy)carbonyl) thieno(3,4-b) thiophenediyl)) (PTB2), poly((4,8-bis(octyl)benzo(1,2-b:4, 5-b')dithiophene-2,6-diyl) (2-((ethylhexyloxy)carbonyl)

thieno(3,4-b)thiophenediyl)) (PTB3), poly((4,8-bis-(ethyl-hexyloxybenzo(1,2-b:4,5-b')dithiophene-2,6-diyl)(2-((octyloxy)carbonyl)-3-fluoro)thieno(3,4-b)thiophenediyl)) (PTB4), poly((4,8-bis(ethylhexyloxybenzo(1,2-b:4,5-b')dithiophene-2,6-diyl)(2-((octyloxy)carbonyl) thieno(3,4-b) thiophenediyl)) (PTB5), poly((4,8-bis(octyloxy)benzo(1,2-b:4,5-b')dithiophene-2,6-diyl)(2-((butyloctyloxy)carbonyl) thieno(3,4-b)thiophenediyl)) (PTB6), poly[[5-(2-ethylhexyl)-5,6-dihydro-4,6-dioxo-4H-thieno[3,4-c]pyrrole-1,3-diyl][4,8-bis[(2-ethylhexyl)oxy]benzo[1,2-b:4,5-b']dithiophene-2,6-diyl]](PBDTTPD), poly[1-(6-{4,8-bis[(2-ethylhexyl)oxy]-6-methylbenzo[1,2-b:4,5-b']dithiophen-2-yl}-3-fluoro-4-methylthieno[3,4-b]thiophen-2-yl)-1-octanone](PBDTTT-CF), and poly[2,1,3-benzothiadiazole-4,7-diyl-2,5-thiophenediyl(9,9-dioctyl-9H-9-silafluorene-2,7-diyl)-2,5-thiophenediyl](PSiF-DBT). Other suitable materials are poly[5,7-bis(4-decanyl-2-thienyl) thieno[3,4-b]diathiazole-thiophene-2,5](PDDTT), poly[2,3-bis(4-(2-ethylhexyloxy)phenyl)-5,7-di(thiophen-2-yl)thieno[3,4-b] pyrazine](PDTTP), and polythieno[3,4-b]thiophene (PTT). In particular embodiments, suitable materials are copolymers derived from substituted or unsubstituted benzodithiophene monomers, such as the PTB1-7 series and PCPDTBT; or benzothiadiazole monomers, such as PCDTBT and PCPDTBT.

In particular embodiments, the donor material is a polymer with a low degree of crystallinity or is an amorphous polymer. Degree of crystallinity may be increased by substituting aromatic rings of the main polymer chain. Long chain alkyl groups containing six or more carbons or bulky polyhedral oligosilsesquioxane (POSS) may result in a polymer material with a lower degree of crystallinity than a polymer having no substituents on the aromatic ring, or having short chain substituents such as methyl groups. Degree of crystallinity may also be influenced by processing conditions and means, including, but not limited to, the solvents used to process the material and thermal annealing conditions. Degree of crystallinity is readily determined using analytical techniques such as calorimetry, differential scanning calorimetry, x-ray diffraction, infrared spectroscopy and polarized light microscopy.

Suitable materials for the acceptor include fullerene derivatives such as [6,6]-phenyl-$C_{61}$-butyric acid methyl ester (PCBM), PCBM analogs such as $PC_{70}BM$, $PC_{71}BM$, $PC_{80}BM$, bis-adducts thereof, such as bis-$PC_{71}BM$, indene mono-adducts thereof, such as indene-$C_{60}$ monoadduct (ICMA) and indene bis-adducts thereof, such as indene-$C_{60}$ bisadduct (ICBA). Fluorene copolymers such as poly[(9,9-dioctylfluorenyl-2,7-diyl)-alt-(4,7-bis(3-hexylthiophen-5-yl)-2,1,3-benzothiadiazole)-2',2"-diyl](F8TBT) may also be used, alone or with a fullerene derivative.

In one embodiment, the first electrode functions as the cathode and the second electrode as the anode. In another embodiment, the first electrode functions as the anode and the second electrode as the cathode. Suitable anode materials include, but are not limited to, metals such as Al, Ag, Au, and Pt; metal oxides such as indium tin oxide (ITO), indium zinc oxide (IZO), and zinc oxide (ZnO); and organic conductors such as p-doped conjugated polymers like PEDOT. Suitable cathode materials include transparent conductive oxides (TCO) and thin films of metals such as gold and silver. Examples of suitable TCO include ITO, IZO, aluminum zinc oxide (AZO), fluorinated tin oxide (FTO), tin oxide ($SnO_2$), titanium dioxide ($TiO_2$), ZnO, indium zinc oxide (In—Zn—O series), indium gallium oxide, gallium zinc oxide, indium silicon zinc oxide, indium gallium zinc oxide, or combinations thereof.

Referring again to FIGS. 1-6, the TFT array may be a two dimensional array of passive or active pixels, which stores charge for read out by electronics, disposed on an active layer formed of amorphous silicon or an amorphous metal oxide, or organic semiconductors. In some embodiments, the TFT array includes a silicon TFT array, an oxide TFT array, an organic TFT, or combinations thereof. Suitable amorphous metal oxides include zinc oxide, zinc tin oxide, indium oxides, indium zinc oxides (In—Zn—O series), indium gallium oxides, gallium zinc oxides, indium silicon zinc oxides, and indium gallium zinc oxides (IGZO). IGZO materials include $InGaO_3(ZnO)_m$ where m is <6) and $InGaZnO_4$. Suitable organic semiconductors include, but are not limited to, conjugated aromatic materials, such as rubrene, tetracene, pentacene, perylenediimides, tetracyanoquinodimethane and polymeric materials such as polythiophenes, polybenzodithiophenes, polyfluorene, polydiacetylene, poly(2,5-thiophenylene vinylene), poly(p-phenylene vinylene), and derivatives thereof.

The TFT array 120 is further disposed on a substrate 170. Suitable substrate 170 materials include glass, ceramics, plastics and metals. The substrate 170 may be present as a rigid sheet such as a thick glass, a thick plastic sheet, a thick plastic composite sheet, and a metal plate; or a flexible sheet, such as, a thin glass sheet, a thin plastic sheet, a thin plastic composite sheet, and metal foil. Examples of suitable materials for the substrate include glass, which may be rigid or flexible; plastics such as polyethylene terephthalate, polybutylene phthalate, polyethylene naphthalate, polystyrene, polycarbonate, polyether sulfone, polyallylate, polyimide, polycycloolefin, norbornene resins, and fluoropolymers; metals such as stainless steel, aluminum, silver and gold; metal oxides such as titanium oxide and zinc oxide; and semiconductors such as silicon. In one particular embodiment, the substrate includes a polycarbonate.

As shown in FIGS. 1-6, the scintillator layer 140, the photodiode 130, and the TFT array 120 are enclosed inside an encapsulation cover 160 to protect them from the moisture and oxygen introduced from the atmosphere. In some embodiments, one or more additional seals 180 may be provided to provide effective sealing between the encapsulation cover 160 and the substrate 170.

In some embodiments of the invention, apart from being protected from the external moisture and oxygen, the photodiode 130 may be further protected from the oxygen that may be introduced (for example, from the scintillator layer 140) during the formation of the x-ray detector or during operation of the x-ray detector. An oxygen getter layer 150 including an ether-containing material may be provided in the organic x-ray detector 100 to provide this protection. As shown in FIGS. 1-6, the oxygen getter layer 150 is disposed between the organic photodiode 130 and the encapsulation cover 160.

Non-limiting examples of suitable ether-containing materials include polyethers, such as, poly(ethylene glycol), poly(propylene glycol), poly(butylene glycol), crown ether, epoxy resin, or combinations thereof. In some embodiments, the ether-containing material may include a polymer that includes a polyether moiety. The polyether moiety may be present as a homopolymer, as a block in a block copolymer, or as a side chain on another polymer (i.e. as a comb polymer). There is no limitation on the polymer morphology, that is, the polymers may be linear, branched, cross-linked, networked, or cyclic. Further, any suitable molecular weight may be used such that a liquid or a solid material can be obtained. Also, as the oxidation mechanism is independent of endgroup chemistry, there is no limitation on endgroup chemistry, and the nature of the two endgroups can be different. For example, one or both endgroups may be hydrogen, methyl, higher alkyl, vinyl, epoxy, thiol, glycidyl, tosylate, or an ester. The ester could be an acrylate or a methacrylate, thereby allowing polymerization of the polyether moiety either by itself or as a mixture with other monomers.

In some embodiments, the ether-containing material includes a poly(alkylene glycol), such as, for example, poly(ethylene glycol), poly(propylene glycol), poly(butylene glycol), or combinations thereof.

In some embodiments, the ether-containing material includes bifunctional ethylene glycol or poly(ethylene glycol). Non-limiting examples of suitable ether-containing materials include:

ethylene glycol diacrylate having a chemical structure (I):

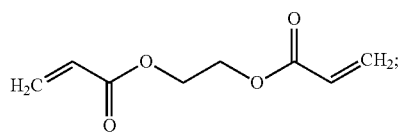

poly(ethylene glycol) diacrylate having a chemical structure (II):

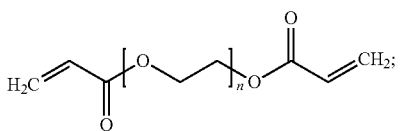

poly(ethylene glycol) diglycidyl ether having a chemical structure (III):

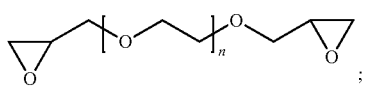

poly(ethylene glycol) dithiol having a chemical structure (IV):

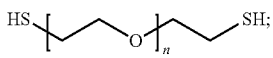

poly(ethylene glycol) divinyl ether having a chemical structure (V):

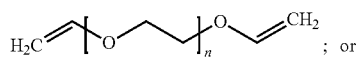

poly(ethylene glycol)-di-tosylate having a chemical structure (VI):

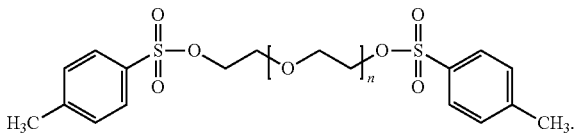

In some embodiments, the ether-containing material may be used in essentially pure form relying on adventitious radicals or x-rays to create the free radicals that can react with oxygen. Alternatively, a catalyst may be further used to generate radicals. Effective catalysts generally have a plurality of oxidation states readily available and include transition metals such as iron, cobalt, and copper.

In some embodiments, the oxygen-getter layer may further include a transition metal catalyst, for example, a cobalt salt, an iron salt, a copper salt, or combinations thereof. The transition metals may be introduced as salts of carboxylic acids to provide good compatibility with the polyether. Non-limiting examples of suitable catalysts include copper acetate, copper octanoate, cobalt acetate, cobalt octanoate, or combinations thereof.

Figure 8:
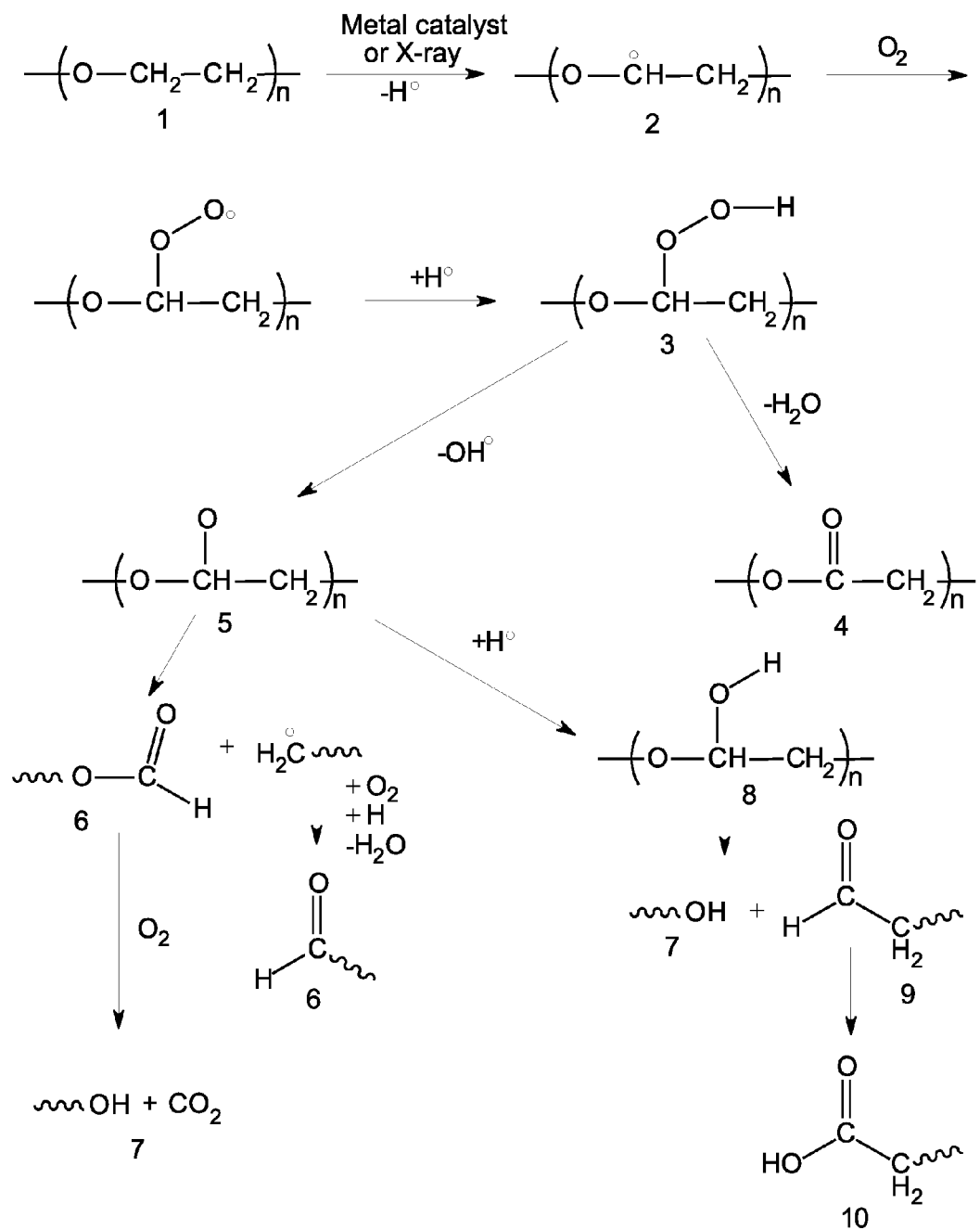
FIG. 8 shows the oxidation pathways for poly(ethylene glycol), according to one embodiment of the invention.

FIG. 8 shows some of the possible oxidation pathways for poly(ethylene glycol), as an example, without being bound by any theory. As shown in FIG. 8, all of the carbon atoms in a poly(alkylene glycol) (PEG) are part of an aliphatic ether structure and, as such, are susceptible to oxidation leading to esters and alcohols as the major products (also described in S. Morlat and J-L. Gardette, *Polymer* (2001) 42 6071-6079). As shown in FIG. 8, the poly(ethylene glycol) repeat unit, 1, loses a hydrogen atom due to a transition metal catalyst or due to the effect of x-rays to form a free radical, 2. The free radical can react with oxygen present to form a hydroperoxy radical that can further abstract a hydrogen atom from an adjacent PEG unit to reform a free radical, 2 and form a hydroperoxide, 3. The hydroperoxide, 3, can lose a molecule of water to form an ester, 4, or undergo O—O bond cleavage to make a hydroxyl radical (.OH) and the oxy radical, 5. The hydroxyl radical can abstract a hydrogen atom from a PEG unit to form water and another free radical, 2. The oxy radical, 5, can undergo β scission to make a formate ester, 6, and an alkyl radical that will react with oxygen to eventually make another formate ester. Formate esters can be further oxidized to make an alcohol, 7, and carbon dioxide. By another pathway, the oxy radical, 6, can abstract a hydrogen atom from a PEG unit to make a hemiacetal, 8, that will decompose to another alcohol, 7, and an aldehyde, 9. Aldehydes readily oxidize to make peroxyacids that eventually produce carboxylic acids, 10. Other pathways may also possible to form other products in minor amounts. It should be noted that each repeat unit can potentially react with at least one molecule of oxygen, such that the absorption capacity per gram of PEG may be 0.73 g (511 cc at STP) of oxygen.

Figure 2:
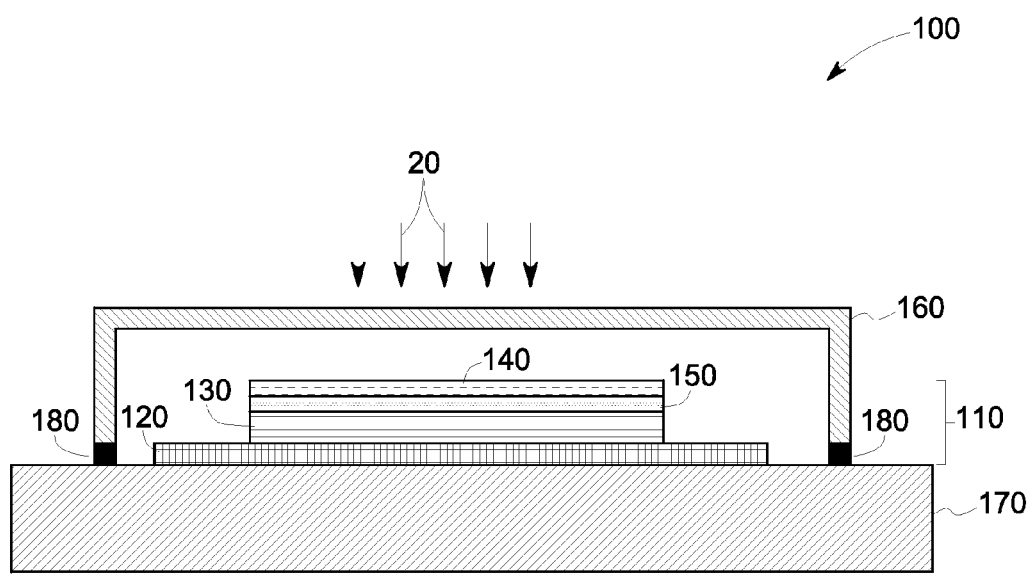
FIG. 2 is a schematic of an organic x-ray detector, according to one embodiment of the invention.

The oxygen-getter layer may have any suitable configuration in the organic x-ray detector such that the oxygen-getter layer is disposed between the organic photodiode and the encapsulation cover. In some embodiments, at least a portion of the oxygen-getter layer may be disposed outside the path of the x-ray radiation. In some embodiments, at least a portion of the oxygen-getter layer may be disposed in the path of the x-ray radiation as shown in FIGS. 1-6. Further, the oxygen getter layer 150 may be a component of the layered structure 110, as shown in FIGS. 1-2. Alternately, the oxygen getter layer 150 may be disposed such that at least a portion of the oxygen getter layer 150 is in contact with the encapsulation cover 160, as show in FIGS. 3-5.

FIG. 1 illustrates an embodiment of an organic x-ray detector 100 wherein the oxygen getter layer 150 is disposed on top of the scintillator layer 140. FIG. 2 illustrates an embodiment of an organic x-ray detector 100 wherein the oxygen getter layer 150 is interposed between the scintillator layer 140 and the organic photodiode 130.

Figure 3:
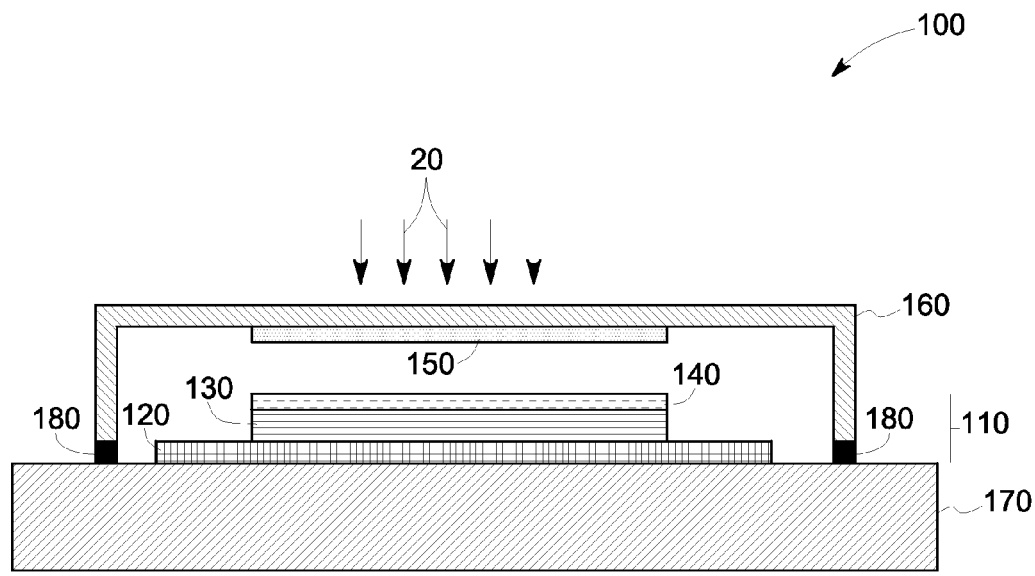
FIG. 3 is a schematic of an organic x-ray detector, according to one embodiment of the invention.
Figure 4:
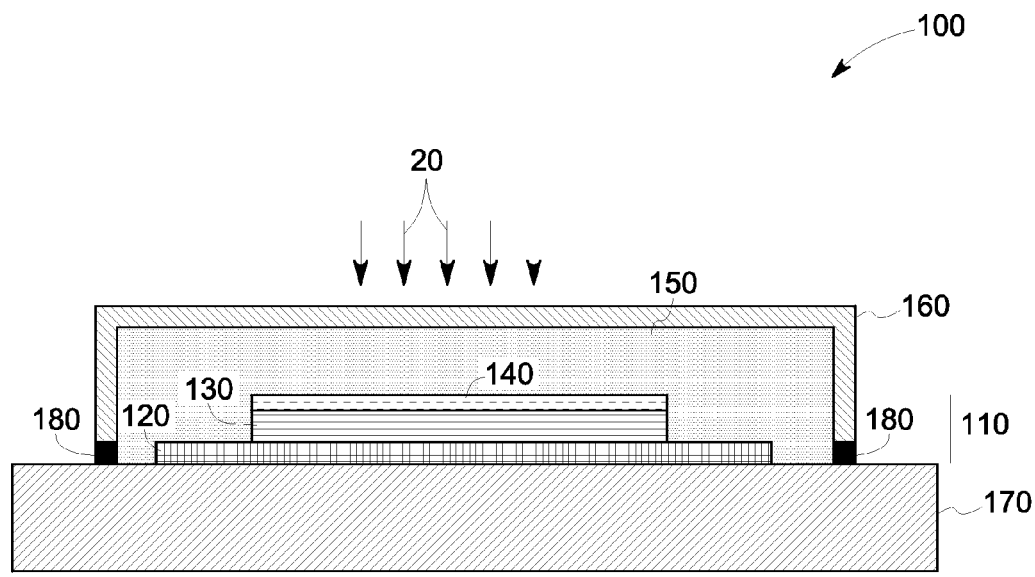
FIG. 4 is a schematic of an organic x-ray detector, according to one embodiment of the invention.
Figure 5:
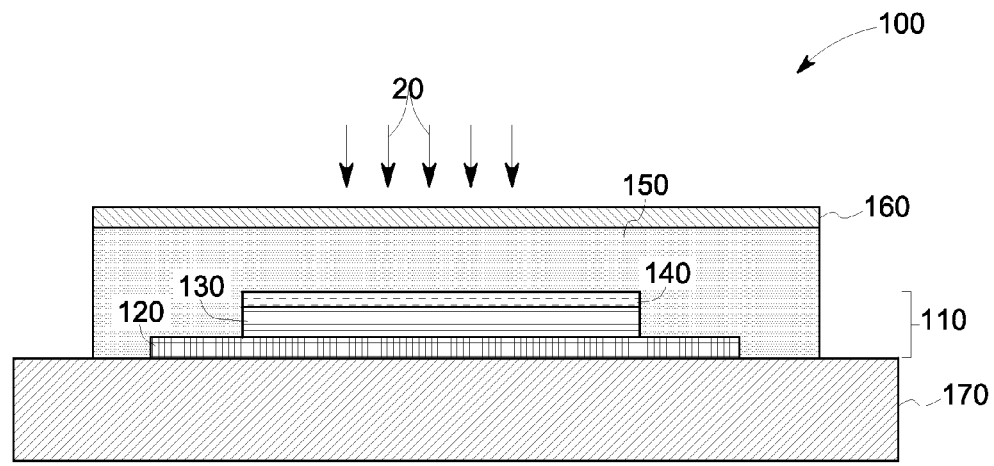
FIG. 5 is a schematic of an organic x-ray detector, according to one embodiment of the invention.

FIG. 3 illustrates an embodiment of an organic x-ray detector 100 wherein the oxygen getter layer 150 is disposed in contact with at least a portion of the encapsulation cover 160. FIGS. 4-5 illustrate embodiments of an organic x-ray detector 100 wherein the oxygen getter layer 150 substantially encapsulates the layered structure 110. In FIG. 4, the encapsulation cover 160 and the seals 180 further provide a sealing arrangement from the outside environment. Alternately, as shown in FIG. 5, the oxygen getter layer 150 itself may provide sealing from the outside environment.

Figure 6:
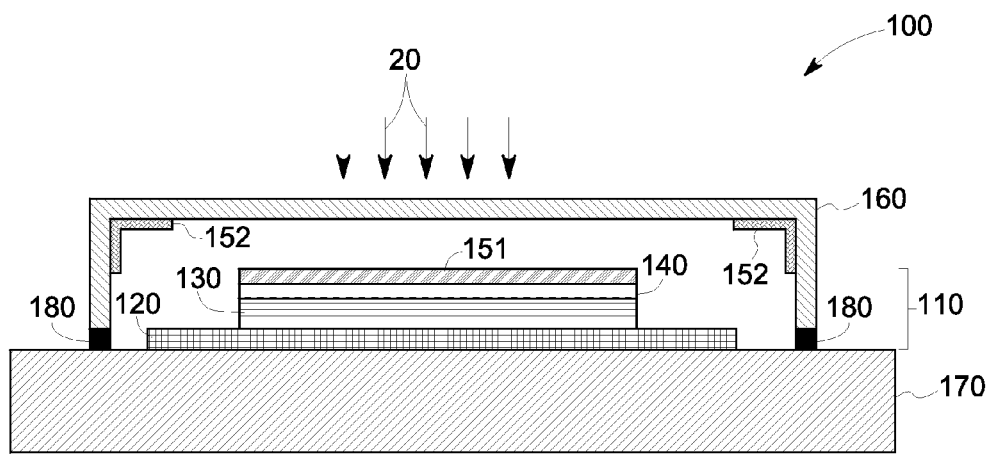
FIG. 6 is a schematic of an organic x-ray detector, according to one embodiment of the invention.

FIG. 6 illustrates another embodiment of an organic x-ray detector including a first getter layer 151 and a second getter layer 152. As shown in FIG. 6, the layered structure 110 includes the first getter layer 151 and the second getter layer 152 is disposed in contact with at least a portion of the encapsulation cover 160.

Without being bound by any theory it is believed that the incorporation of the oxygen-getter layer may improve device reliability by trapping oxygen that otherwise can degrade performance of the device.

Figure 9:
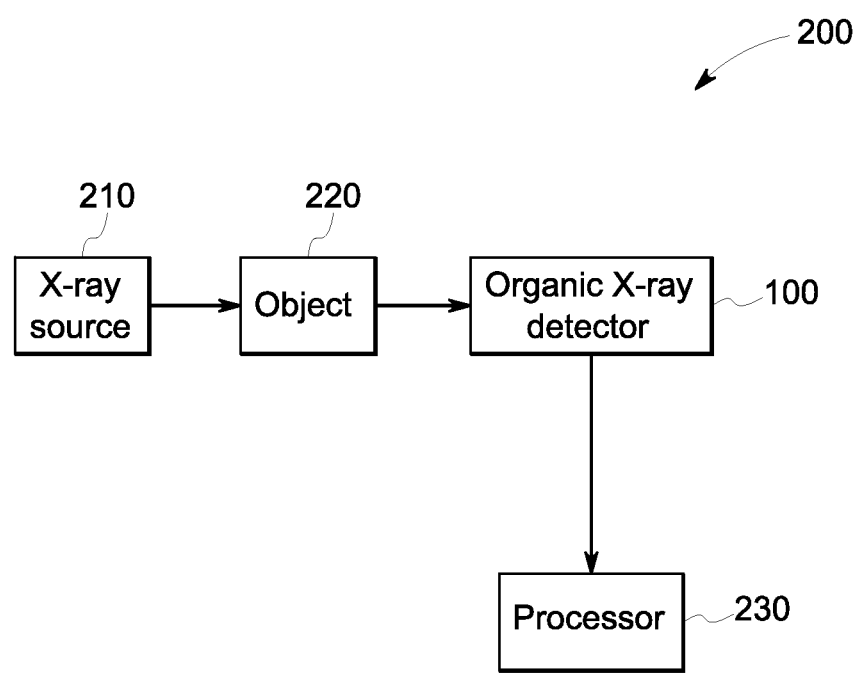
FIG. 9 is schematic of an x-ray system, according to one embodiment of the invention.
Figure 10A:
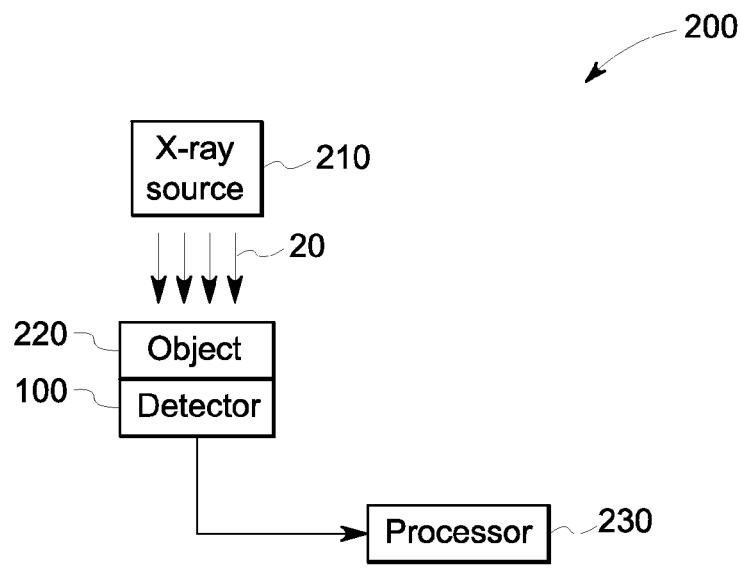
FIG. 10A is schematic of an x-ray system, according to one embodiment of the invention.
Figure 10B:
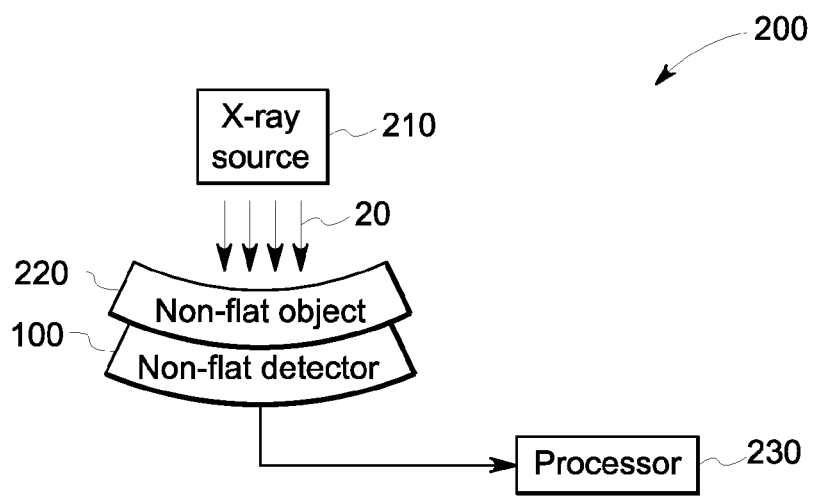
FIG. 10B is schematic of an x-ray system, according to one embodiment of the invention.

In some embodiments, an x-ray system is also presented. As shown in FIG. 9, the x-ray system 200 includes an x-ray source 210 configured to irradiate an object 220 with x-ray radiation; an organic x-ray detector 100 as described earlier, and a processor 230 operable to process data from the organic x-ray detector 100. FIGS. 10A and 10B further show embodiments of the x-ray system suitable for substantially flat objects or objects with a curved shape. As shown in FIGS. 10A and 10B, the x-ray detector 100 may have a shape suitable for the object 220. In FIGS. 10A and 10B, the processor 230 may be communicatively coupled to the x-ray detector 100 using a wired or a wireless connection.

An x-ray detector according to embodiments of the present invention may be used in imaging systems, for example, in conformal imaging, with the detector in intimate contact with the imaging surface. For parts with internal structure, the detector may be rolled or shaped to contact the part being imaged. Applications for the organic x-ray detectors according to embodiments of the present invention include security imaging; medical imaging; and industrial and military imaging for pipeline, fuselage, airframe and other tight access areas.

EXAMPLES

Example 1

Poly(Ethylene Glycol) Oxygen Uptake

Oxygen uptake setup: Samples were added to 25 mL stainless steel sample cylinders (Swagelok SS-4CS-TW-25) equipped with a ⅜" to ⅛" reducing union (Swagelok SS-600-6-2). The cylinders were attached to a ball valve (Swagelok SS-41GS2) with approx. 12" (30.5 cm) of ⅛" stainless steel tubing. The volume of the cylinder and tubing was determined by evacuating the tube to <0.05 Torr and refilling with air from a gas buret. The gas buret was made in-house from a standard 50 mL buret by attaching a spherical ground glass joint to the top and replacing the stopcock with a 90° bend and barb for tubing. The buret was connected to the leveling bulb with Tygon tubing and filled with low viscosity silicone oil. The manifold had a 3-way stopcock at each end and a tube in the middle. One stopcock could be used for filling with nitrogen or other gas by connecting to a low pressure/low flow gas line and a bubbler tube. The other end had a spherical ground glass joint to fit the buret. The center tube was adapted to fit the valve of the stainless steel vial assembly.

Poly(ethylene glycol) (PEG-600) having a formula (I), and purchased from Aldrich 202401 was used as received.

(I)

Cobalt(II) acetate tetrahydrate (21 mg), purchased from Aldrich 208396, was dissolved in 5.00 g of melted PEG 600 to make a solution with 0.1% Co(II) ions by weight. Small amounts (~10 mg) were weighed into stainless steel vials and sealed either in air or pure oxygen, and the vials were suspended in an 85° C. oven. Periodically, the gas consumption was determined by cooling the vials to room temperature, measuring the volume change using a gas buret, and refilling the vial with fresh air or oxygen. Volumes were corrected for changes in atmospheric pressure and room temperature. Oxygen uptake was conducted for two samples (Samples 1-2) against air and one sample (Sample 3) against oxygen. Table 1 shows the oxygen uptake for Samples 1-3. As shown in Table 1, all three samples showed oxygen uptake.

TABLE 1

| Oxygen uptake for poly(ethylene glycol) | |
|---|---|
| Sample No. | Oxygen uptake (cc/mg) |
| 1 | 0.15 |
| 2 | 0.15 |
| 3 | 0.30 |

Example 2

Poly(Ethylene Glycol) Diacrylate Oxygen Uptake

Example 2 was performed in the same manner as Example 1, except PEG600 was replaced with a bifunctional ether-containing material, Sartomer SR610, which is a poly (ethylene glycol) 600 diacrylate having formula (II):

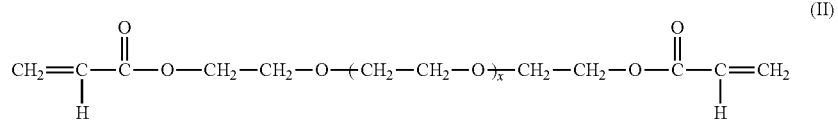

(II)

Sartomer SR610 containing 0.1% Co(II) ions was prepared by dissolving 21 mg of cobalt(II) acetate tetrahydrate in ~0.5 mL methanol and adding the solution to 5.0 g of Sartomer SR610. The solution was stirred magnetically while a stream of nitrogen was blown onto the surface until the flask reached constant weight (~4 hours), indicating that the entire methanol had evaporated. The material was stored under nitrogen until use.

For a UV-cured SR610 film, 1 wt % Irgacure 819 was dissolved in a solution of SR610 and catalyst for two hours at 60° C. Using a pipette, 200 µl of the solution was dispensed on a Teflon film followed by disposing another Teflon substrate on top to squeeze out the solution. UV light was irradiated on top of the sandwiched SR610 for a few seconds, and a thin film of cured SR610 was produced. After carefully peeling the film off the Teflon substrate, an additional 15 min of UV radiation was applied to the film. The fabrication of the UV-cured SR610 free standing film was conducted entirely in a nitrogen-filled glove box.

UV-cured SR610 films were produced using no catalyst (Sample 4), Cu(II) acetate (Sample 5), and Co(II) acetate (Sample 6). Samples 4 and 5 were subjected to oxygen uptake at 85° C. in air, and no measurable uptake was noted after >100 hours. Table 2 shows the oxygen uptake for Samples 4-6. As shown in Table 2, a Co(II)-type catalyst may be required for oxygen uptake in a cured bifunctional getter material.

TABLE 2

Oxygen uptake for poly(ethylene glycol) diacrylate

| Sample No. | Oxygen uptake (cc/mg) |
|---|---|
| 4 | No measurable uptake after 100 hrs |
| 5 | No measurable uptake after 100 hrs |
| 6 | 1.5 cc |

Example 3 and Comparative Example 1

Organic X-Ray Detector Imager with and without Oxygen Getter

Two organic x-ray imagers were fabricated as follows: Glass based thin-film-transistor (TFT) array pre-coated with ITO was used as the substrate. A layer of hole-transport material was deposited onto ultraviolet-ozone treated TFT array substrates via spin-coating, and then baked on a hotplate. An absorber layer consisting of a fullerene based acceptor and a donor material was then spin-coated atop the hole-transport layer, inside a $N_2$ purged glove box. The imager fabrication was completed with ITO sputtering. A DRZ-Plus scintillator (Mitsubishi Chemical) comprised of gadolinium sulfoxylate doped with terbium (Gd2O2S:Tb) was laminated to the imager using a pressure sensitive adhesive (PSA) film from 3M under the product name of 8191L. An x-ray detector imager without the oxygen getter layer was fabricated (Comparative Example 1) by encapsulating the assembly using a cover glass and an edge sealant. An x-ray detector imager with the oxygen getter layer was fabricated (Example 3) in a similar manner, with the additional step of attaching a SR610:Co(II)-based oxygen getter layer (prepared in Example 2) to the inner side of the cover glass.

Reliability of the imagers was then tested under 85° C./85% relative humidity. Performance was characterized using an x-ray imager functional tester. After 525 hours, the averaged dark leakage current at the edge of the Comparative Example 1 increased from <0.01 $nA/cm^2$ to 0.17 $nA/cm^2$. In contrast, the averaged dark leakage current at the edge of the Example 3 increased from <0.01 $nA/cm^2$ to 0.03 $nA/cm^2$. Thus, x-ray detector imagers with the oxygen getter layer exhibited improved reliability when compared to x-ray detector imagers without the oxygen getter layer.

The foregoing examples are merely illustrative, serving to exemplify only some of the features of the invention. The appended claims are intended to claim the invention as broadly as it has been conceived and the examples herein presented are illustrative of selected embodiments from a manifold of all possible embodiments. Accordingly, it is the Applicants' intention that the appended claims are not to be limited by the choice of examples utilized to illustrate features of the present invention. As used in the claims, the word "comprises" and its grammatical variants logically also subtend and include phrases of varying and differing extent such as for example, but not limited thereto, "consisting essentially of" and "consisting of." Where necessary, ranges have been supplied; those ranges are inclusive of all sub-ranges there between. It is to be expected that variations in these ranges will suggest themselves to a practitioner having ordinary skill in the art and where not already dedicated to the public, those variations should where possible be construed to be covered by the appended claims. It is also anticipated that advances in science and technology will make equivalents and substitutions possible that are not now contemplated by reason of the imprecision of language and these variations should also be construed where possible to be covered by the appended claims.

The invention claimed is:

1. An organic x-ray detector, comprising:
   a layered structure comprising:
      a thin-film transistor (TFT) array disposed on a substrate,
      an organic photodiode disposed on the TFT array, and
      a scintillator layer disposed on the organic photodiode;
   an encapsulation cover at least partially encapsulating the layered structure; and
   an oxygen getter layer disposed between the organic photodiode and the encapsulation cover, wherein the oxygen getter layer comprises an oxygen getter material selected from polyalkylene glycols and crown ethers.

2. The organic x-ray detector of claim 1, wherein the oxygen getter material comprises poly(ethylene glycol), poly(propylene glycol), poly(butylene glycol), crown ether, or combinations thereof.

3. The organic x-ray detector of claim 1, wherein the oxygen getter layer further comprises a catalyst.

4. The organic x-ray detector of claim 3, wherein the catalyst comprises a salt of a transition metal.

5. The organic x-ray detector of claim 3, wherein the catalyst comprises a cobalt salt.

6. The organic x-ray detector of claim 3, wherein the catalyst comprises copper acetate, copper octanoate, cobalt acetate, cobalt octanoate, or combinations thereof.

7. The organic x-ray detector of claim 1, wherein the layered structure comprises the oxygen getter layer.

8. The organic x-ray detector of claim 7, wherein the oxygen getter layer is interposed between the organic photodiode and the scintillator layer.

9. The organic x-ray detector of claim 7, wherein the oxygen getter layer is disposed on the scintillator layer.

10. The organic x-ray detector of claim 1, wherein the oxygen getter layer substantially encapsulates the layered structure.

11. The organic x-ray detector of claim 1, wherein the oxygen getter layer is disposed in contact with at least a portion of the encapsulation cover.

12. The organic x-ray detector of claim 1, comprising a first getter layer and a second getter layer, wherein the layered structure comprises the first getter layer and the second getter layer is disposed in contact with at least a portion of the encapsulation cover.

13. The organic x-ray detector of claim 1, wherein the substrate comprises a material selected from the group consisting of glass, metal foil, plastic, and combinations thereof.

14. The organic x-ray detector of claim 1, wherein the TFT array comprises a silicon TFT array, an oxide TFT array, an organic TFT, or combinations thereof.

15. An organic x-ray detector, comprising:
a layered structure comprising:
a thin-film transistor (TFT) array disposed on a substrate,
an organic photodiode disposed on the TFT array, and
a scintillator layer disposed on the organic photodiode;
an encapsulation cover at least partially encapsulating the layered structure; and
an oxygen getter layer disposed between the organic photodiode and the encapsulation cover, wherein the oxygen getter layer comprises a transition metal catalyst and an oxygen getter material selected from polyalkylene glycols and crown ethers.

16. An x-ray system, comprising:
an x-ray source;
an organic x-ray detector comprising:
a layered structure comprising:
a thin-film transistor (TFT) array disposed on a substrate,
an organic photodiode disposed on the TFT array, and
a scintillator layer disposed on the organic photodiode;
an encapsulation cover at least partially encapsulating the layered structure; and
an oxygen getter layer disposed between the organic photodiode and the encapsulation cover, wherein the oxygen getter layer comprises an oxygen getter material selected from polyalkylene glycols and crown ethers; and
a processor operable to process data from the organic x-ray detector.

17. The x-ray system of claim 16, wherein the oxygen getter material comprises poly(ethylene glycol), poly(propylene glycol), poly(butylene glycol), crown ether, or combinations thereof.

18. The x-ray system of claim 16, wherein the oxygen getter layer further comprises a salt of a transition metal.

19. The x-ray system of claim 16, wherein the layered structure comprises the oxygen getter layer.

20. The x-ray system of claim 16, wherein the oxygen getter layer substantially encapsulates the layered structure.

21. The x-ray system of claim 16, wherein the oxygen getter layer is disposed in contact with at least a portion of the encapsulation cover.

* * * * *